United States Patent [19]

Toge et al.

[11] Patent Number: 5,552,389
[45] Date of Patent: Sep. 3, 1996

[54] SUPPRESSORY COMPOSITIONS AGAINST HEPATIC METASTASES OF TUMORS

[75] Inventors: Tetsuya Toge; Toshihiro Hirai; Akihiro Yoshimoto, all of Hiroshima; Kenichi Yoshida, Ibaraki, all of Japan

[73] Assignee: Senju Pharmaceutical Co., Ltd., Osaka, Japan

[21] Appl. No.: 410,842

[22] Filed: Mar. 27, 1995

[30] Foreign Application Priority Data

Mar. 29, 1994 [JP] Japan .................................. 6-058671
Oct. 4, 1994 [JP] Japan .................................. 6-240167

[51] Int. Cl.⁶ ........................ A61K 31/70; A61K 31/665
[52] U.S. Cl. ............................................. 514/25; 514/100
[58] Field of Search .................................... 514/100, 25

[56] References Cited

PUBLICATIONS

Patent Abstracts of Japan, vol. 014 No. 543, Nov. 30, 1990 & JPA02229168, Sep. 11, 1990 Abstract.
Patent Abstracts of Japan, vol. 014, No. 543, Nov. 30, 1990 JPA02229169, Sep. 11, 1990 Abstract.
Database WPI, Week 8731, Derwent Publications Ltd, London, GB., AN87–218325 & JP–A 62145019 (Senju Seiyaku KK), Dec. 19, 1985 (abstract).
Arzneimittelforschung, vol. 42, No. II, 1992, pp. 1072–1074 In Vitro Studies on the Influence of L–Ascorbic Acid . . . Phospholipase A2 Activity.
Proceedings of the Annual Meeting of the American Association for Cancer Research, vol. 34, Mar. 1993, pp. 570–571, Kohn, E. C. et al. 'Signal Transduction Therapy of Metastasis'.

*Primary Examiner*—Jerome D. Goldberg
*Attorney, Agent, or Firm*—Burgess, Ryan and Wayne

[57] ABSTRACT

The present invention provides suppressory compositions against hepatic metastases of tumors which comprise a phosphoric acid diester compound of the formula:

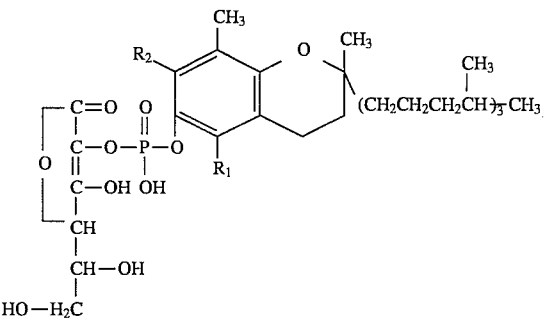

(wherein $R_1$ and $R_2$ each is the same as or different from the other and represents hydrogen or methyl) or a pharmacologically acceptable salt thereof.

1 Claim, 4 Drawing Sheets

SUPPRESSORY COMPOSITIONS AGAINST HEPATIC METASTASES OF TUMORS

BACKGROUND OF THE INVENTION

1) Field of the Invention

The present invention relates to useful suppressory compositions against hepatic metastases of tumors. In more detail, this invention relates to suppressory compositions against hepatic metastases of tumors which comprise a phosphoric acid diester compound of ascorbic acid and tocopherol or a pharmacologically acceptable salt thereof.

2) Background Art

At present, remarkable progress has been made in the treatment of malignant tumors (cancers) in terms of the pharmacotherapy, surgical therapy, radiation therapy, etc., but no effective preventive measure is available against cancer metastasis, or an Indicator of cancer malignancy. In the sector of cancer treatment, therefore, there is strongly demanded the development of an improved suppressory composition against cancer metastasis. Cancer metastasis is roughly classified into hematogenous metastasis and lymphatic metastasis, and the establishment of cancer metastasis is required to proceed through the sequential steps of (1) infiltrative and destructive proliferation of tumor cells at the primary site, (2) segregation Of tumor cells or cell colonies, (3) migration of tumor cells, (4) fixation or establishment and (5) proliferation at the site of fixation. The cancer metastasis is involved particularly in such organs as the lung, liver and digestive organs, and the present inventors, with a specific view to a search for an improved cancer-metastasis suppressory composition, have conducted extensive research studies on the mechanism of cancer metastasis, inclusive of the pulmonary metastasis of cancers.

In a series of such research studies, the present inventors carried out investigation into the hepatic metastases of malignant tumors: intensive research was performed on the basis of the hypothesis that the level of intrahepatic or liver lipid peroxide (LPO) would rise due to surgical invasion, or a stress, and in turn damage the vascular endothelia, resulting in enhanced hematogeneous metastases to the liver of malignant tumors. As a result, the experiments with the hepatic metastasis model revealed that the surgical invasion promotes the hepatic metastases of tumors and elevates the level of liver lipid peroxide. The novel finding was followed by further research to seek for an improved suppressory composition against hepatic metastases of tumors, thus leading the present inventors to the discovery that a kind of phosphoric acid diester compounds suppresses effectively not only elevation of the level of liver lipid peroxide but also nodulation of tumors on the liver surface and could provide a promising suppressory composition against hepatic metastases of malignant tumors. This has culminated into the present invention.

DESCRIPTION OF THE PREFERRED EMBODIMENT

The present invention provides useful suppressory compositions against hepatic metastases of tumors which comprise a phosphoric acid diester compound.

Thus, the present invention relates to suppressory compositions against hepatic metastases of tumors which comprise a phosphoric acid diester compound represented by the following formula:

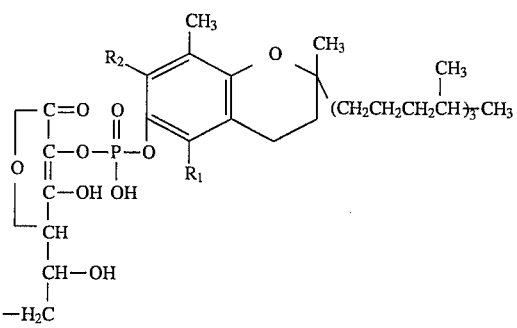

(wherein $R_1$ and $R_2$ each is the same as or different from the other and represents hydrogen or methyl), or a pharmacologically acceptable salt thereof (hereinafter referred to collectively as "Present Compounds").

The Present Compounds that are intended for use as a suppressory composition against hepatic metastases of tumors according to the present invention can suitably be synthesized for example by the methods as described in Japanese Patent Publication No. Hei 2-44478 (1990) and Japanese Unexamined Patent Publication No. Sho B2-205091 (1982) or methods similar thereto.

The Present Compounds that are usable as a suppressory composition against hepatic metastases of tumors according to the present invention are already known to find application in a wide variety of fields, such as an anti-cataract agent, prophylactic and therapeutic agent for climacteric disorders, cosmetic exhibiting skin-beautifying activity (Japanese Patent Publication No. Hei 2-44478 (1990)), an antiimflammatory agent (Japanese Patent Publication No. Hei 1-277044) and antiulcer agent (Japanese Unexamined Patent Publication No. Sho 88-270828 (1988)) as well as a prophylactic and therapeutic drug for ischemic diseases of the organs (Japanese Unexamined Patent Publication No. Hei 2-111722 (1990)). However, It has never been known In the past that the Present Compounds are useful as a suppressory composition against hepatic metastases of tumors.

The Present Compounds that are useful as a suppressory composition against hepatic metastases of tumors according to the present invention can suitably be utilized in the form of either free acid or pharmacologically acceptable salt for the objective of this invention. As the pharmacologically acceptable salt, there may be exemplified alkali metal salts, such as sodium and potassium salts, and alkaline earth metal salts, such as calcium and magnesium salts, but any salts other than these can also suitably be employed only if they are pharmacologically acceptable salts.

The suppressory compositions against hepatic metastases of tumors according to the present invention can be formulated with one or not less than two of the Present Compounds in suitable combination, depending upon the intended purpose and necessity.

The Present Compounds that are employable as an active agent for the suppressory compositions against hepatic metastases of tumors according to the present invention exhibit extremely lowered toxicity and improved safety, and can advantageously be utilized for the objective of this invention. [For example, potassium salt of a phosphoric acid diester of L-ascorbic acid and DL-α-tocopherol (hereinafter referred to briefly as "EPC-K") shows $LD_{50}$ values of 5 g/kg p.o. (in rats) and not less than 100 mg/k i.v. (in rats)].

The suppressory compositions against hepatic metastases of tumors according to the present invention can suitably be used orally or parenterally (for example, by way of intravenous injection, subcutaneous injection, intramuscular injection and drip infusion). Referring to the dosage form, the suppressory compositions against hepatic metastases of tumors can suitably be processed and formulated by conventional methods in either dosage form of solid preparations such as tablets, granules, powders and capsules and liquid preparations, such as injectable solutions. These pharmaceutical preparations may suitably be incorporated with a variety of conventionally used additives, such as excipients, binders, disintegrating agents, dispersants, reabsorption promoters, buffers, surfactants, solubilizers, preservatives, emulsifiers, isotonizing agents, stabilizers and pH regulating agents.

In cases where the Present Compounds are used as a suppressory composition against hepatic metastases of tumors, their doses vary depending upon the type of the compounds used, the age, body weight and sex of patients and the symptoms of diseases as well as the type of dosage forms. And the Present Compounds are desirably administered to human adults at a single dose in the range of about 0.5 to 200 mg, preferably about 2 to 50 mg, once a day in the case of injectable solutions, and at a single dose in the range of about 5 to 2,000 mg, preferably about 20 to 500 several times a day In the case of preparations for internal use.

Unless contrary to the objective of this invention, the suppressory compositions against hepatic metastases of tumors according to the present invention may be incorporated with another suppressory compositions against hepatic metastases of tumors and/or other active agents capable of producing different medicinal effects.

BRIEF DESCRIPTION OF THE DRAWINGS

Described below are the examples and preparation examples to illustrate this invention in more detail, but the present invention is not understood to be limited by these examples, wherein referring to the drawings attached hereto.

Example 1

Experiments on hepatic metastasis of tumor in relation to a level of liver lipid peroxide:

Using a model of hepatic metastasis of tumor, an experiment was conducted to determine a correlation of hepatic metastasis of tumor with a level of liver lipid peroxide (LPO). In addition, an experiment was effected on the Present Compound in terms of its suppressory effect of liver lipid peroxide (LPO) and suppressory effect on hepatic metastasis of tumor.

Method;

Male Donryu rats (ca. 10-weeks aged) were employed as an experimental animal, while AH60C cells (derived from rat hepatoma) were used as a tumor cell. The rats were divided into three groups, namely a laparothoractomy group (Group LT) undergoing intratracheal intubation, followed by thoraco-laparotomy for one hour, a laparotomy group (Group L) undergoing only laparotomy for one hour and a control group (Group C) undergoing laparotomy, followed by immediate closure of the abdomen. The rats were subjected to laparotomy under anesthesia with ether and Ketalar and given $5 \times 10^5$ of AH60C cells through the portal vein to inflict surgical invasion, followed by laparotomy three weeks later to determine the number of tumor nodules on the liver surface. In addition to this, the serum samples were drawn, while the liver and lung tissues were isolated, on Disease Days 1. 2 and 3 to determine their respective levels of lipid peroxide by the TBA method.

Then, the LT group was subdivided into a group treated an hour before surgical invasion with the Present Compound through intravenous injection of EPC-K at a dose of 5 mg/kg (Group EPC-K) and a group not treated with the Present Compound (Group C) to determine levels of liver lipid peroxide 24 hours later as well as numbers of tumor nodules on the liver surface 3 weeks later. Test of data was done by Mann-Whitney U method.

Figure 1:
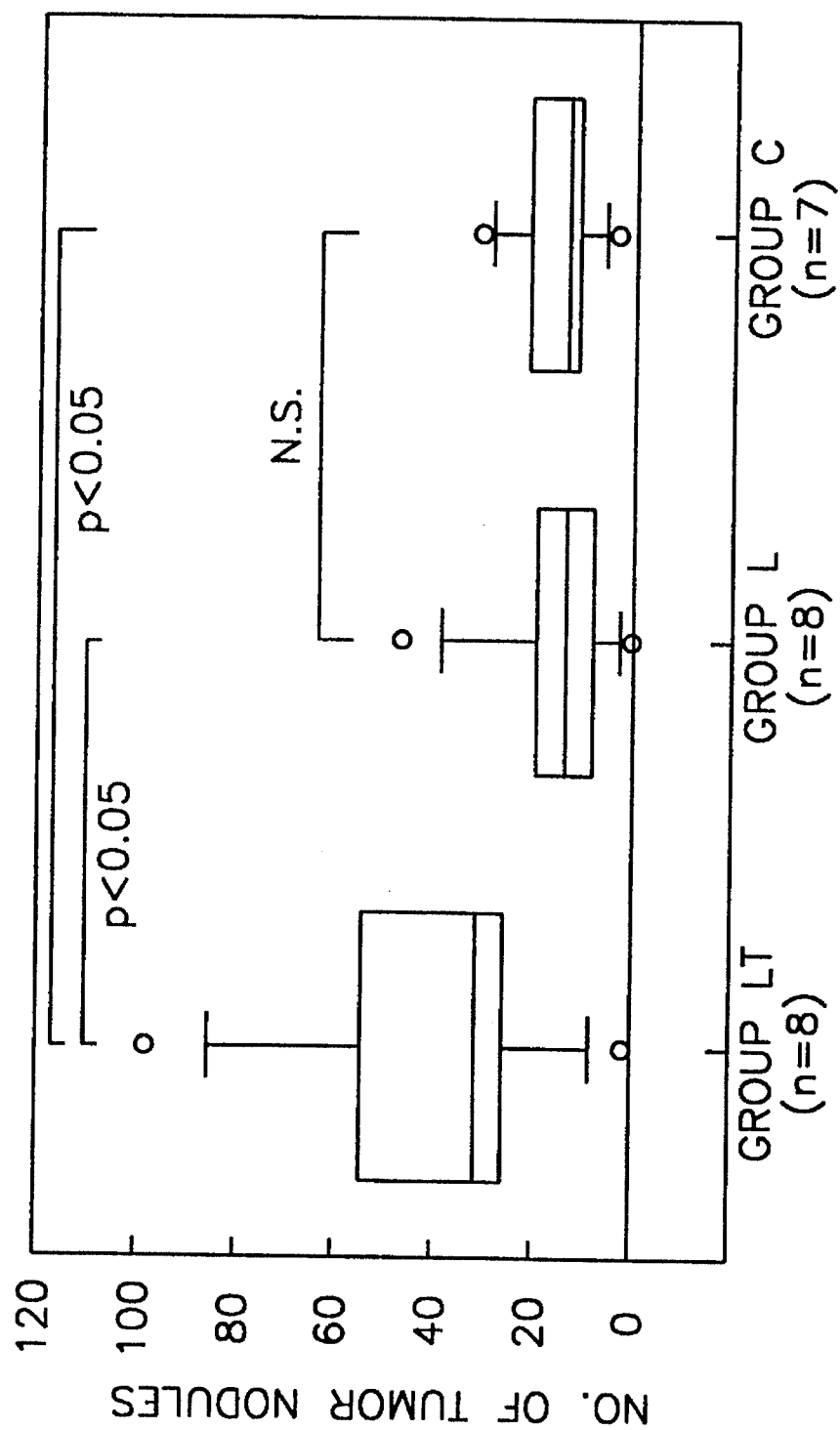
FIG. 1 is a graph showing the numbers of tumor nodules on the liver surface (plotted on the ordinate) as found in the group undergoing laparothoractomy (Group LT), group undergoing laparotomy (Group L) and control group (Group C), respectively.

Result:

The number of tumor nodules on the liver surface was found to be $40.6 \pm 29.7$ in Group LT, $15 \pm 15.8$ in Group L and $13.7 \pm 9.4$ in Group C, respectively (Refer to FIG. 1). Group LT showed significant difference ($p<0,05$) against Groups L and C.

Figure 2:
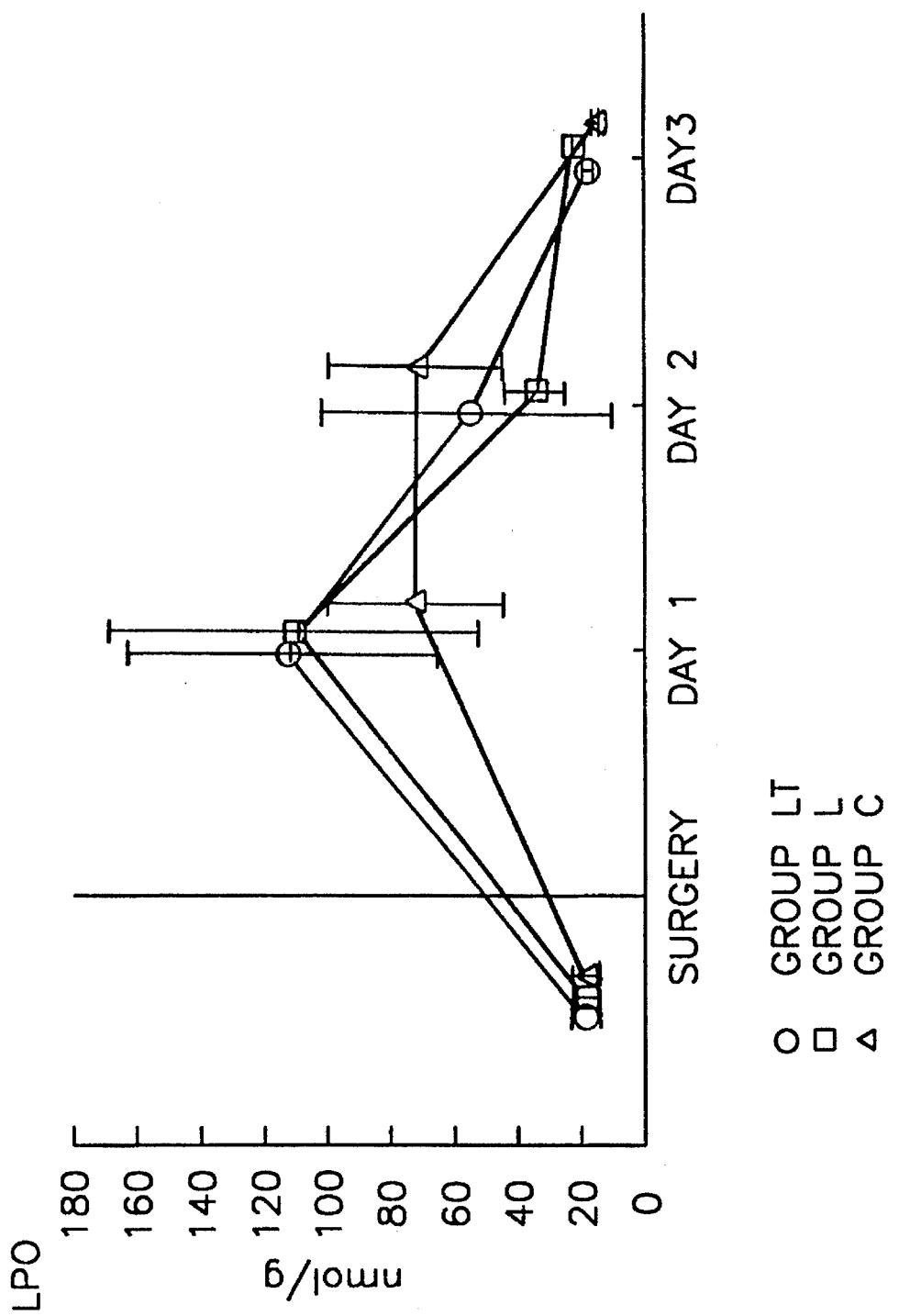
FIG. 2 is a graph showing changes in level of liver lipid peroxide (LPO, nmol/g; plotted on the ordinate) as found in the group undergoing laparothoractomy (Group LT), group udergoing laparotomy (Group L) and control group (Group C), respectively.

The level of liver lipid peroxide was found to be $16.6 \pm 3.8$ nmol/g (n=4) in Group C, which figure was taken as a prior value. The surgical invasion raised the levels of intrahepatic lipid peroxide, which reached the peaks on Disease Day 1; $93.9 \pm 22.5$ nmol/g in Group LT, $102.3 \pm 53.6$ nmol/g in Group L and $66.9 \pm 25.5$ nmol/g in Group C (refer to FIG. 2). There was not observed any significant difference between Groups LT and C, while Group LT displayed tendency toward elevated level of liver lipid peroxide. On Disease Day 3, the levels were found in three groups to return nearly to the prior value. However, the lipid peroxide levels in the serum and lung remained unchanged, with no difference being noted among these three animal groups.

Figure 3:
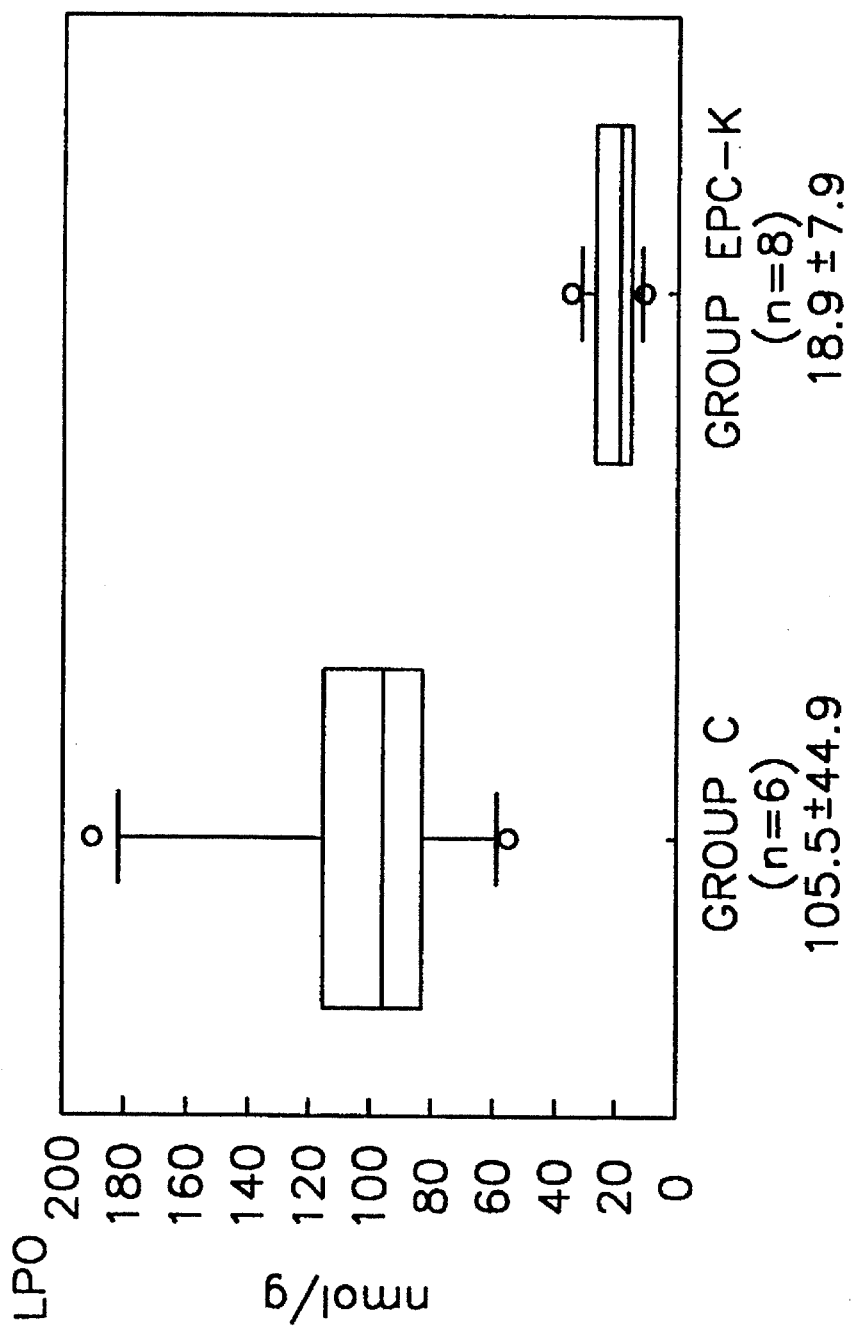
FIG. 3 is a graph showing levels of intrahepatic lipid peroxide (LPO, nmol/g; plotted on the ordinate) as determined 24 hours after surgical invasion (laparothoractomy) inflicted in the group not treated through administration of the Present Compound (Group C) and group treated through administration of the Present Compound (Group EPC-K), respectively.
Figure 4:
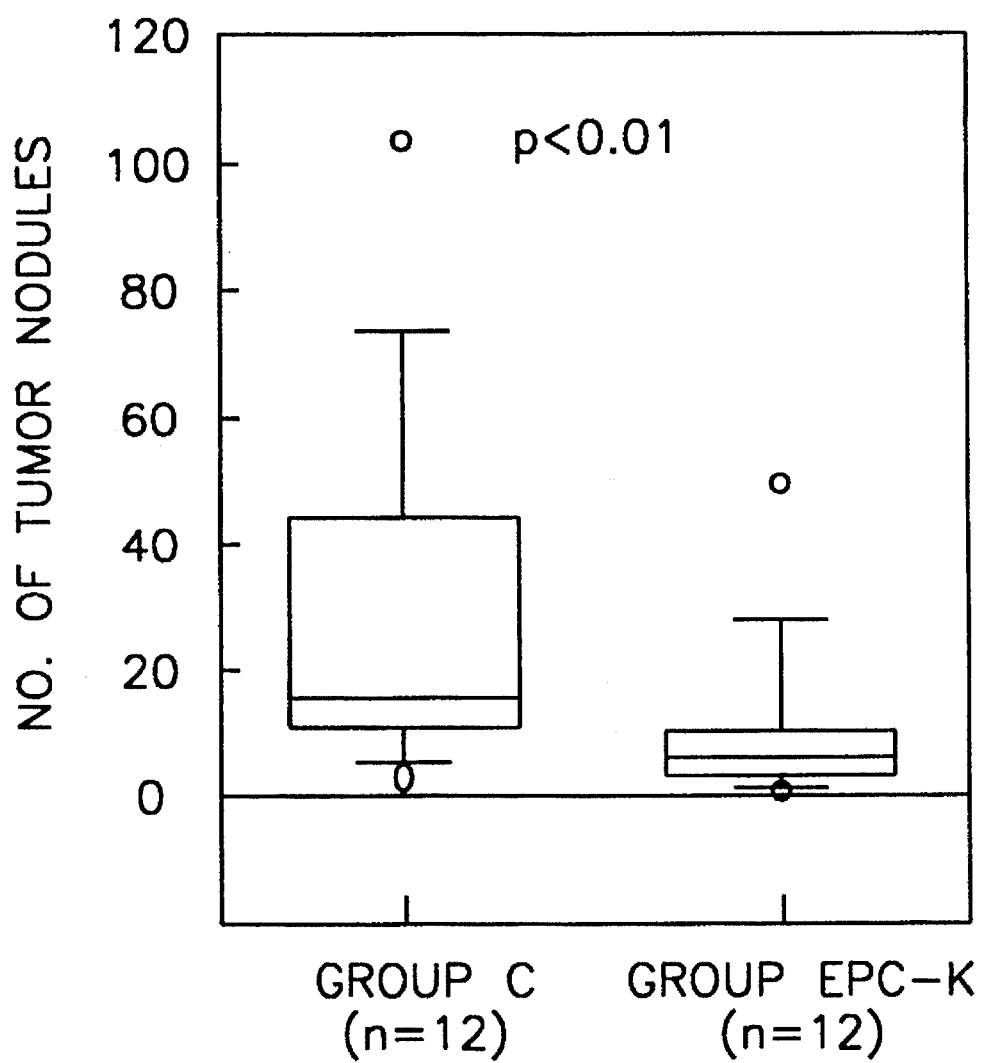
FIG. 4 is a graph showing the numbers of tumor nodules on the liver surface (plotted on the ordinate) as determined 3 weeks later in the group not treated through administration of the Present Compound (Group C) and group treated through administration of the Present Compound (Group EP-CK). respectively.

Prior administration of EPC-K at a dose of 5 mg/kg caused the level of liver lipid peroxide 24 hours later to decrease to $18.9 \pm 17.9$ nmol/g, leading to significantly suppressed elevation of the level ($p<0.05$) (refer to FIG. 3), while this reduced the numbers of tumor nodules on the liver surface down to $8.9 \pm 12.7$ in Group EPC-K and $27.2 \pm 30.0$ in Group C (not treated), with significant suppression being noted in Group EPC-K ($p<0.01$) (refer to FIG. 4).

Conclusion:

The surgical invasion, a kind of stress, raised the number of tumor nodules on the liver surface (hepatic metastasis) and also increased the level of liver lipid peroxide. The Present Compound suppressed both an elevation in level of liver lipid peroxide and an increase in tumor nodulation on the liver surface and was proven to constitute a prospective suppressory composition against hepatic metastases of tumors.

Preparation Example 1

Tablet for internal use:

| | |
|---|---|
| EPC-K | 100 mg |
| Lactose | 75 mg |
| Starch | 20 mg |
| Polyethylene glycol 6000 | 5 mg |

The above-described ingredients are mixed and processed into a tablet by the conventional procedure. Sugar coating may be provided to the table if necessary.

Formulation Example 2

Injectable solution:

| | |
|---|---|
| EPC-K | 200 mg |
| Mannitol | 5.0 g |
| 1N-Sodium hydroxide | q.s. |
| Distilled water | To make the total up to 100 ml (pH 6.5) |

The above-described ingredients are mixed and sterile-filtered by the conventional procedure. The filtrate is filled sterile in 5 ml portions into glass ampoules, followed by fusing to give an injectable solution.

The pharmaceutical preparations of this invention suppress effectively an elevation in level of liver lipid peroxide and also an increase in tumor nodulation on the liver surface, and are consequently useful as a suppressory composition against hepatic metastases of tumors.

We claim:

1. A method of suppressing hepatic metastases of tumors which comprises administering to a human subject in need of such method a pharmaceutically effective amount of phosphoric acid diester compound of the formula:

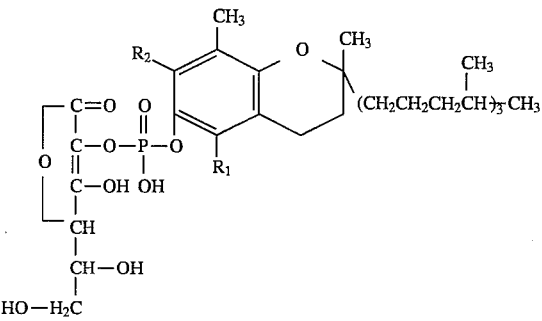

wherein $R_1$ and $R_2$ each is the same as or different from the other and represents hydrogen or methyl or a pharmacologically acceptable salt thereof.

* * * * *